(12) United States Patent
Basu et al.

(10) Patent No.: US 12,396,787 B2
(45) Date of Patent: Aug. 26, 2025

(54) CATHETER WITH INTEGRATED THIN-FILM MICROSENSORS

(71) Applicant: Biosense Webster (Israel) Ltd., Yokneam (IL)

(72) Inventors: Shubhayu Basu, Anaheim, CA (US); Dustin R. Tobey, San Dimas, CA (US); Pieter E. Van Niekerk, Monrovia, CA (US); Cesar Fuentes-Ortega, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 159 days.

(21) Appl. No.: 17/109,266

(22) Filed: Dec. 2, 2020

(65) Prior Publication Data

US 2021/0220042 A1 Jul. 22, 2021

Related U.S. Application Data

(60) Provisional application No. 62/962,360, filed on Jan. 17, 2020.

(51) Int. Cl.
*A61B 18/14* (2006.01)
*A61B 18/00* (2006.01)
*A61B 18/12* (2006.01)

(52) U.S. Cl.
CPC .............. *A61B 18/1492* (2013.01); *A61B 2018/00345* (2013.01); *A61B 2018/00577* (2013.01);
(Continued)

(58) Field of Classification Search
CPC ...... A61B 18/1492; A61B 2018/00345; A61B 2018/0057; A61B 2018/00761;
(Continued)

(56) References Cited

U.S. PATENT DOCUMENTS

| 5,853,409 A | 12/1998 | Swanson et al. |
| 8,956,353 B2 | 2/2015 | Govari et al. |

(Continued)

FOREIGN PATENT DOCUMENTS

| JP | S53-93683 A | 8/1978 |
| JP | H07-194608 A | 8/1995 |

(Continued)

OTHER PUBLICATIONS

International Search Report and Written Opinion dated Jul. 15, 2021, for International Application No. PCT/IB2021/050059, 19 pages.

(Continued)

*Primary Examiner* — Jennifer Pitrak McDonald
*Assistant Examiner* — Megan T Fedorky
(74) *Attorney, Agent, or Firm* — Frost Brown Todd LLP

(57) ABSTRACT

An apparatus includes a catheter body and an end effector. The catheter body has a distal end and is sized and configured to fit within regions of a cardiovascular system. The end effector is at the distal end of the catheter body and is sized and configured to fit within regions of a cardiovascular system. The end effector includes an end effector body, an electrode, and a sensor. The end effector body has an outer surface. The electrode has a tissue contact surface. The sensor has a tissue contact surface. The sensor is configured to sense at least one condition associated with tissue contacting the tissue contact surface of the sensor. The tissue contact surface of the sensor is configured to protrude relative to one or both of the outer surface of the end effector body member or the tissue contact surface of the electrode.

20 Claims, 8 Drawing Sheets

(52) U.S. Cl.
CPC ............... *A61B 2018/00761* (2013.01); *A61B 2018/00767* (2013.01); *A61B 2018/00791* (2013.01); *A61B 2018/00875* (2013.01); *A61B 2018/126* (2013.01)

(58) Field of Classification Search
CPC ........... A61B 2018/00767; A61B 2018/00791; A61B 2018/00875; A61B 2018/126
See application file for complete search history.

(56) References Cited

U.S. PATENT DOCUMENTS

| | | | |
|---|---|---|---|
| 9,480,416 | B2 | 11/2016 | Govari et al. |
| 2006/0030833 | A1* | 2/2006 | Harris ................. A61B 5/6852 600/509 |
| 2013/0030426 | A1 | 1/2013 | Gallardo et al. |
| 2017/0079738 | A1 | 3/2017 | Botzer et al. |
| 2018/0071017 | A1 | 3/2018 | Bar-tal et al. |
| 2018/0185090 | A1* | 7/2018 | Coates ............... A61B 18/1492 |
| 2018/0325399 | A1* | 11/2018 | Stewart .................. A61B 18/18 |
| 2019/0038347 | A1* | 2/2019 | Panescu ................ A61B 5/068 |

FOREIGN PATENT DOCUMENTS

| | | |
|---|---|---|
| JP | 2009-513270 A | 4/2009 |
| JP | 2017-534408 A | 11/2017 |
| JP | 2019-193790 A | 11/2019 |

OTHER PUBLICATIONS

Japanese Office Action, Notification of Reasons for Refusal and Search Report by Registered Search Organization, dated Jul. 30, 2024 for Application No. JP 2022-543484, 26 pgs.

Japanese Office Action, Notification of Reasons for Refusal, dated Dec. 10, 2024 for Application No. JP 2022-543484, 2 pgs.

Chinese First Office Action and Search Report dated Jul. 2, 2025, for Application No. 202180009393.0, 13 pages.

* cited by examiner

US 12,396,787 B2

CATHETER WITH INTEGRATED THIN-FILM MICROSENSORS

PRIORITY

This application claims priority to U.S. Provisional Pat. App. No. 62/962,360, entitled "Catheter with Integrated Thin-Film Microsensors," filed Jan. 17, 2020, the disclosure of which is incorporated by reference herein, in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2018/0071017, entitled "Ablation Catheter with a Flexible Printed Circuit Board," published Mar. 15, 2018, the disclosure of which is incorporated by reference herein, in its entirety; and U.S. Pat. No. 8,956,353, entitled "Electrode Irrigation Using Micro-Jets," issued Feb. 17, 2015, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia.

When using an ablation catheter, it may be desirable to ensure that the one or more electrodes of the ablation catheter are sufficiently contacting target tissue. For instance, it may be desirable to ensure that the one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. OVERVIEW OF EXEMPLARY ABLATION CATHETER SYSTEM

Figure 1:
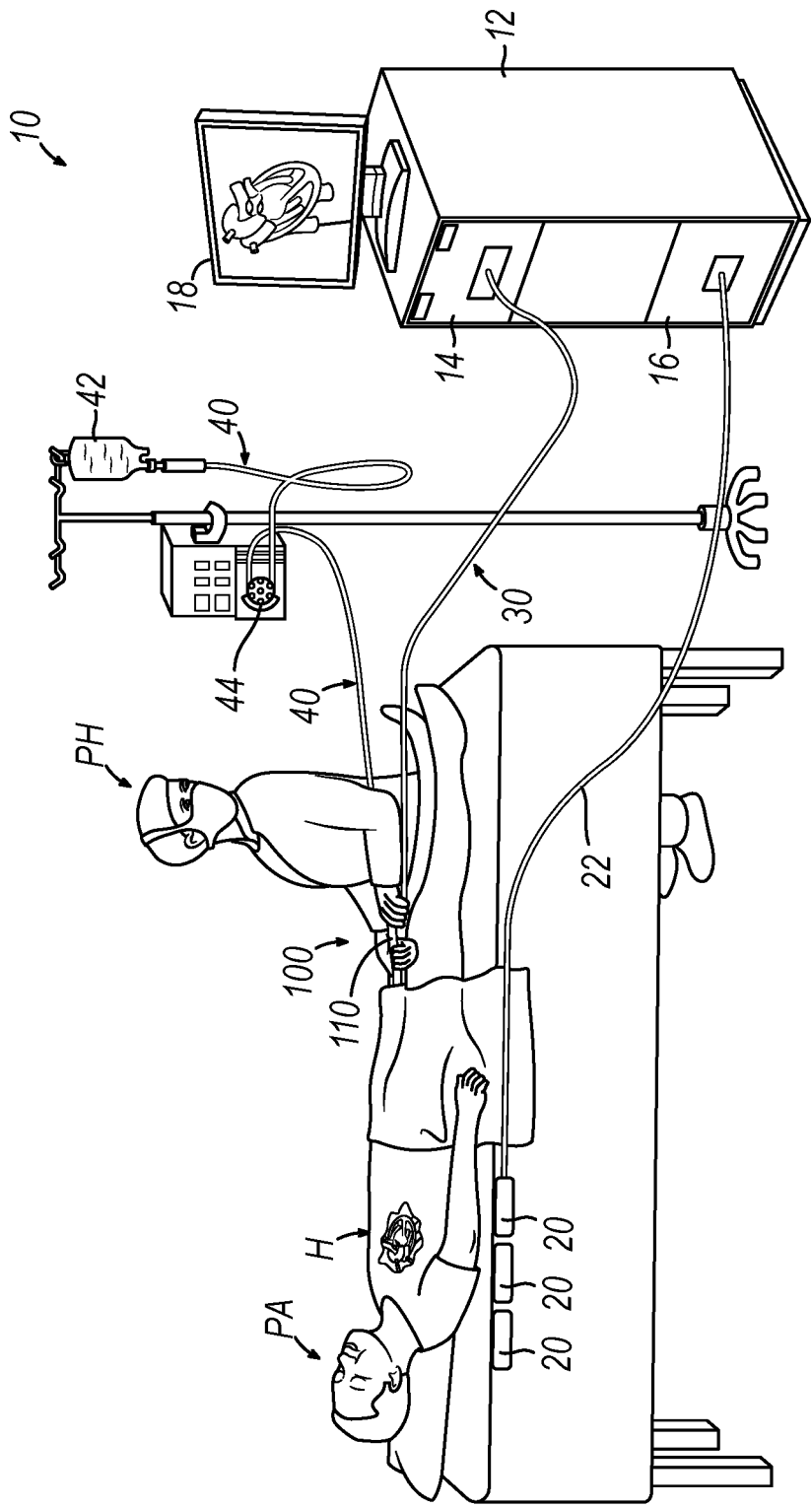
FIG. 1 depicts a schematic view of a medical procedure in which a catheter of a catheter assembly is inserted in a patient.
Figure 2:
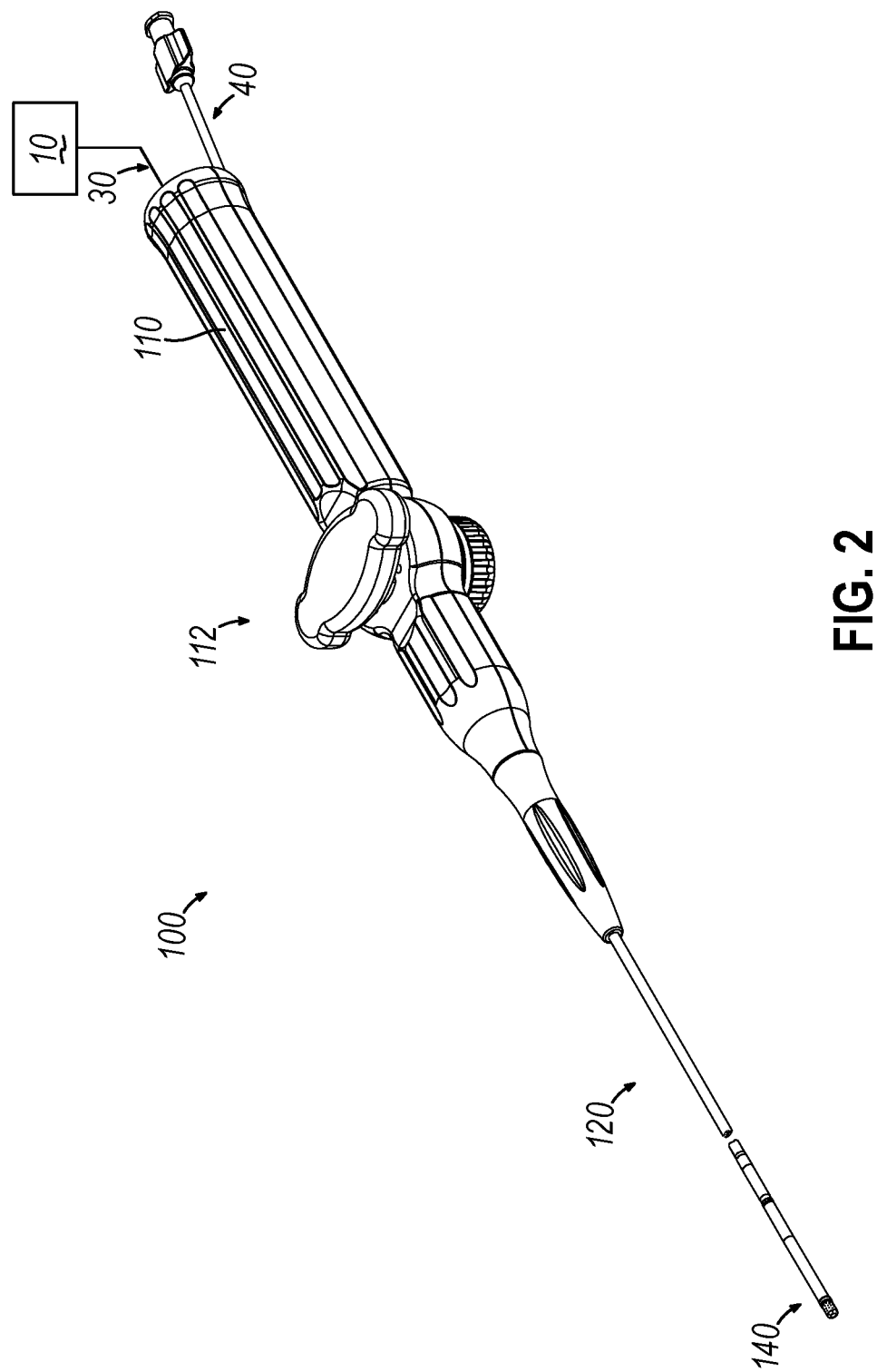
FIG. 2 depicts a perspective view of the catheter assembly of FIG. 1, with additional components shown in schematic form.

FIG. 1 shows an exemplary medical procedure and associated components of a cardiac ablation catheter system that may be used to provide cardiac ablation as referred to above. In particular, FIG. 1 shows a physician (PH) grasping a handle (110) of a catheter assembly (100), with an end effector (140) of a catheter (120) (shown in FIGS. 2-3 but not shown in FIG. 1) of catheter assembly (100) disposed in a patient (PA) to ablate tissue in or near the heart (H) of the patient (PA). As shown in FIG. 2, catheter assembly (100) includes handle (110), catheter (120) extending distally from handle (110), end effector (140) located at a distal end of catheter (120), and a deflection drive assembly (112) associated with handle (110).

As will be described in greater detail below, end effector (140) includes various components configured to deliver RF energy to targeted tissue sites, provide EP mapping functionality, track external forces imparted on end effector (140), track the location of end effector (140), and disperse irrigation fluid. As will also be described in greater detail below, deflection drive assembly (112) is configured to deflect end effector (140) and a distal portion of catheter (120) away from a central longitudinal axis (L-L) (FIGS. 3-5) defined by a proximal portion of catheter (120).

Figure 3:
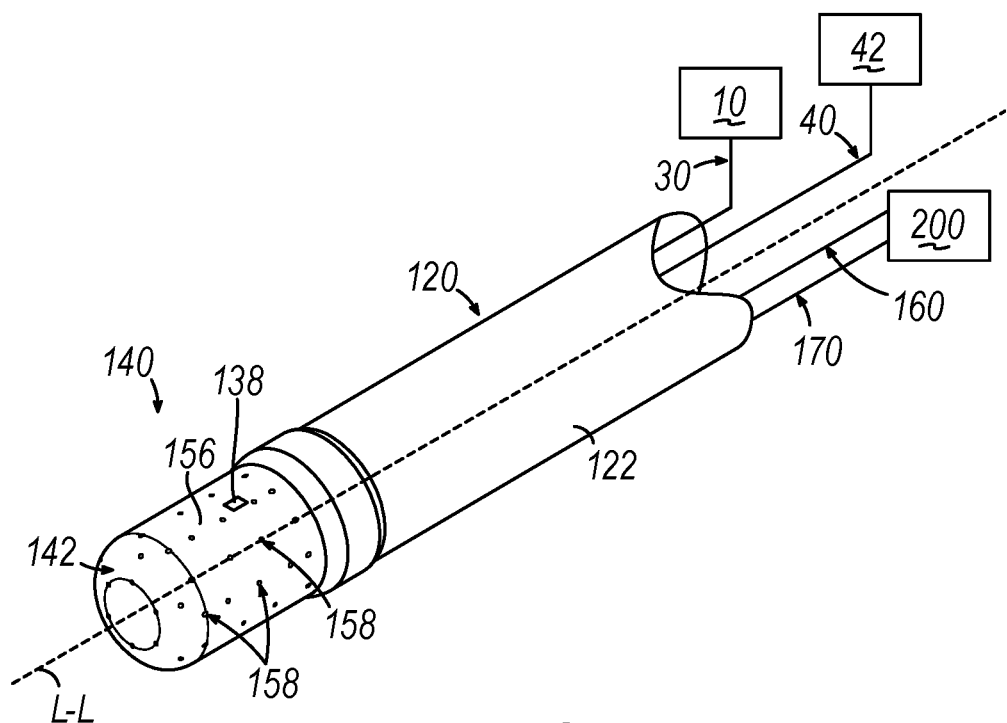
FIG. 3 depicts a perspective view of a distal portion of the catheter of FIG. 1, with additional components shown in schematic form.

As shown in FIG. 3, catheter (120) includes an elongate flexible sheath (122), with end effector (140) being disposed at a distal end of elongate flexible sheath (122). End effector (140) and various components that are contained in elongate flexible sheath (122) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrodes (138) of end effector (140) as described in greater detail below. Console (12) includes a processor (not shown) that processes such EP mapping signals and thereby provides EP mapping as is known in the art.

First driver module (14) of the present example is further operable to provide RF power to a distal tip member (142) of end effector (140), as will be described in greater detail below, to thereby ablate tissue. Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

First driver module (14) is also operable to receive position indicative signals from a position sensor assembly (150) in end effector (140). In such versions, the processor of console (12) is also operable to process the position indicative signals from position sensor assembly (150) to thereby determine the position of end effector (140) within the patient (PA). As will be described in greater detail below, position sensor assembly (150) includes a pair of coils on respective panels (151) that are operable to generate signals that are indicative of the position and orientation of end effector (140) within the patient (PA). The coils are configured to generate electrical signals in response to the presence of an alternating electromagnetic field generated by field generators (20). Other components and techniques that may be used to generate real-time position data associated with end effector (140) may include wireless triangulation, acoustic tracking, optical tracking, inertial tracking, and the like. Alternatively, end effector (140) may lack a position sensor assembly (150).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from position sensor assembly (150) of end effector (140). For instance, as end effector (140) of catheter (120) moves within the patient (PA), the corresponding position data from position sensor assembly (150) may cause the processor of console (12) to update the patient anatomy views in display (18) in real time to depict the regions of patient anatomy around end effector (140) as end effector (140) moves within the patient (PA). Moreover, the processor of console (12) may drive display (18) to show locations of aberrant conductive tissue sites, as detected via electrophysiological (EP) mapping with end effector (140) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (140) on the images of the patient's anatomy, such as by superimposing an illuminated dot, a crosshair, a graphical representation of end effector (140), or some other form of visual indication. Such a superimposed visual indication may also move within the images of the patient anatomy on display (18) in real time as the physician moves end effector (140) within the patient (PA), thereby providing real-time visual feedback to the operator about the position of end effector (140) within the patient (PA) as end effector (140) moves within the patient (PA). The images provided through display (18) may thus effectively provide a video tracking the position of end effector (140) within a patient (PA), without necessarily having any optical instrumentation (i.e., cameras) viewing end effector (140). In the same view, display (18) may simultaneously visually indicate the locations of aberrant conductive tissue sites detected through EP mapping. The physician (PH) may thus view display (18) to observe the real time positioning of end effector (140) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through openings (158) of distal tip member (142) of end effector (140). Such irrigation may be provided in any suitable fashion as will be apparent to those skilled in the art in view of the teachings herein.

II. EXAMPLE OF END EFFECTOR OF CATHETER ASSEMBLY

Figure 4:
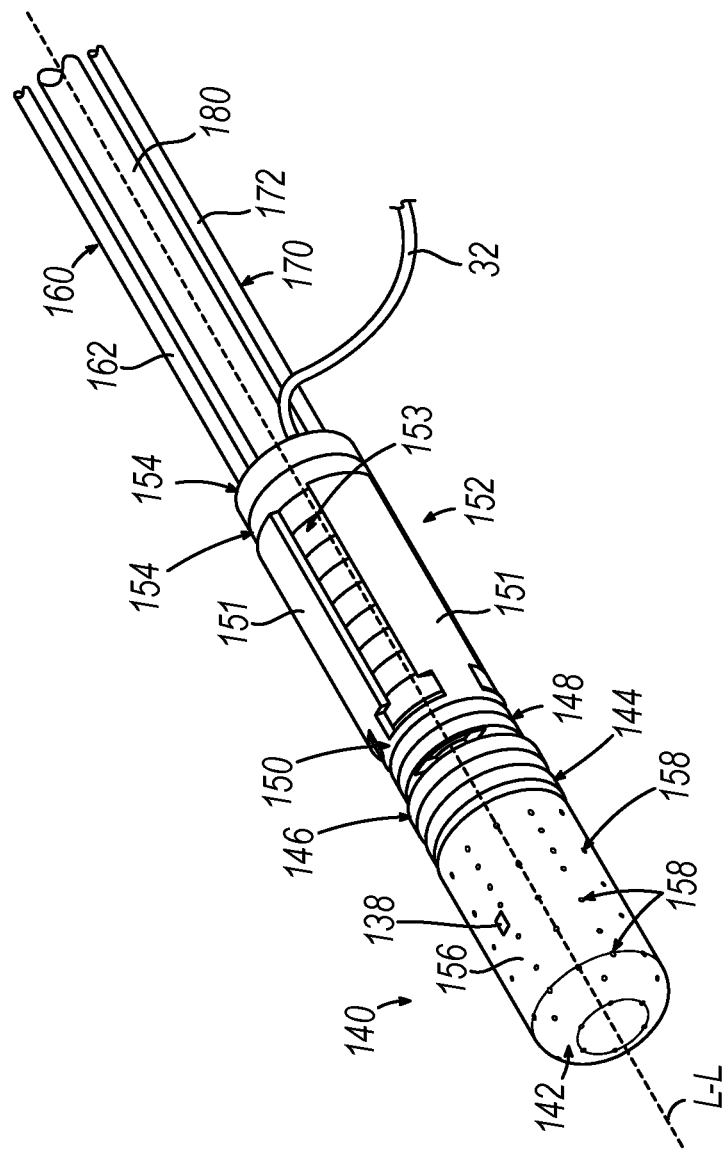
FIG. 4 depicts a perspective view of the distal portion of the catheter of FIG. 1, with an outer sheath omitted to reveal internal components.
Figure 5:
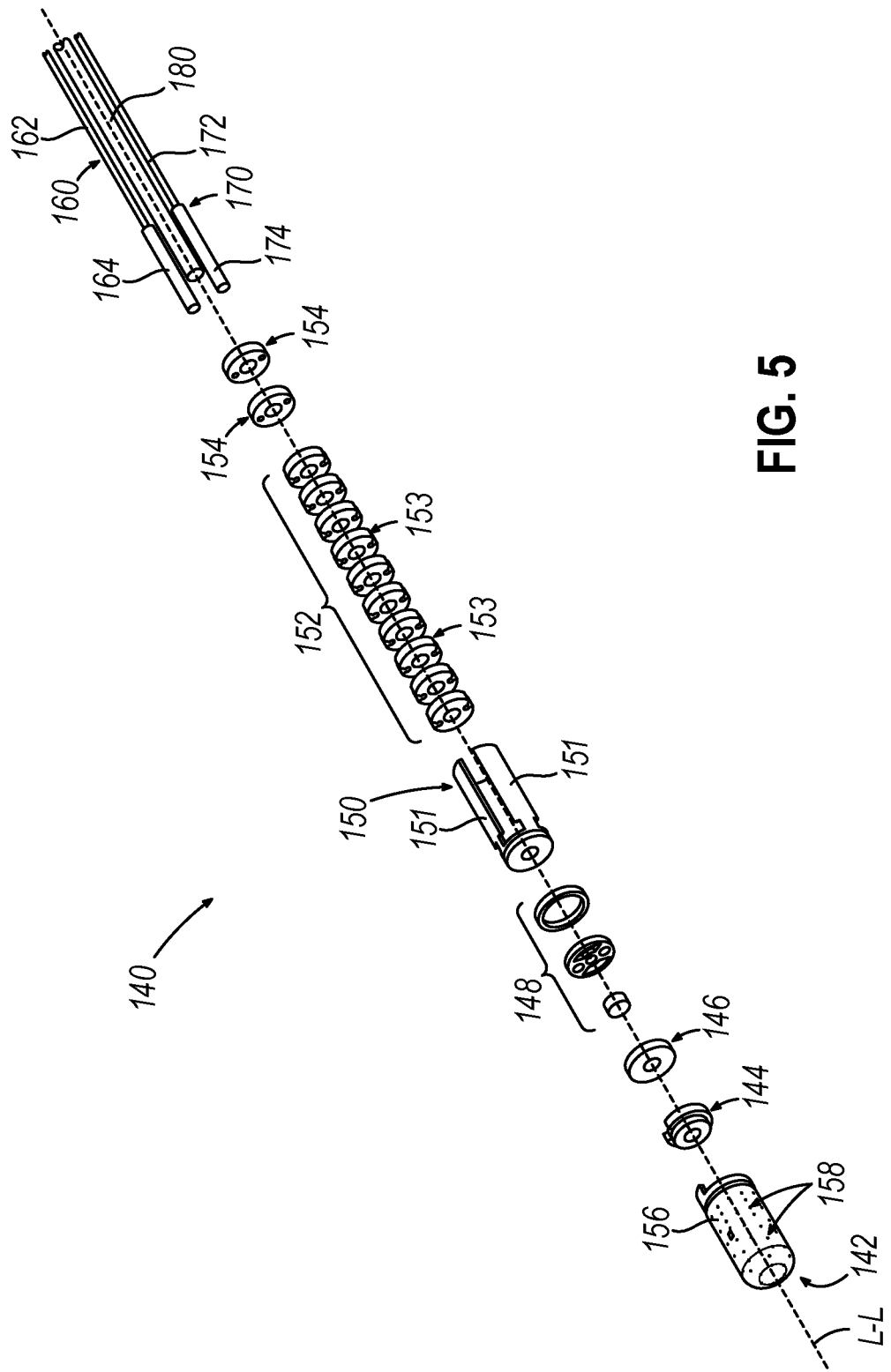
FIG. 5 depicts an exploded perspective view of the distal portion of the catheter of FIG. 1.

As mentioned above, end effector (140) includes various components configured to deliver RF energy to targeted tissue sites, provide EP mapping functionality, track external forces imparted on end effector (140), track the location of end effector (140) within the patient (PA), and disperse irrigation fluid. FIGS. 3-5 show examples of components of end effector (140), and other components of the distal portion of catheter (120), in greater detail. End effector (140) includes a distal tip member (142), a distal tip base (144), a distal circuit disk (146), a force sensor assembly (148), a position sensor assembly (150), a distal spacer stack (152), and a pair of proximal spacers (154). Distal tip member (142), distal tip base (144), distal circuit disk (146), force sensor assembly (148), position sensor assembly (150), distal spacer stack (152), and proximal spacers (154) are coaxially aligned with each other and are stacked longitudinally so that these components (144-154) define a stacked circuit. A pair of push-pull cables (160, 170) and an irrigation tube (180) extend along the length of catheter (120) to reach end effector (140). Each of the foregoing components will be described in greater detail below. Flexible sheath (122) surrounds all of the foregoing components except for distal tip member (142).

As shown in FIGS. 4-5, distal tip member (142) of the present example includes a cylindraceous body (156) with a dome tip. Cylindraceous body (156) and the dome tip may be formed of an electrically conductive material, such as metal. A plurality of openings (158) are formed through cylindraceous body (156) and are in communication with the hollow interior of distal tip member (142). Openings (158) thus allow irrigation fluid to be communicated from the interior of distal tip member (142) out through cylindraceous body (156). Cylindraceous body (156) and the dome tip are also operable to apply RF electrical energy to tissue to thereby ablate the tissue. Such RF electrical energy may be communicated from first driver module (14) to the proximal-most spacer (154) via cable (30). Distal tip member (142) may also include one or more thermocouples that are configured to provide temperature sensing capabilities.

As shown in FIGS. 3-4, distal tip member (142) of the present example also includes one or more EP mapping microelectrodes (138) mounted to cylindraceous body (156). EP mapping microelectrodes (138) are configured to pick up electrical potentials from tissue that comes into contact with EP mapping microelectrodes (138). EP mapping microelectrodes (138) may thus be used to determine locations of aberrant electrical activity in tissue within a cardiovascular anatomical structure (e.g., pulmonary vein, etc.). Signals picked up by EP mapping microelectrodes (138) may be communicated through vias or other structures in the layers that are proximal to force sensor assembly (148), eventually reaching first driver module (14) of console (12) via cable (30). First driver module (14) may process the EP mapping signals and provide the physician (PH) with corresponding feedback indicating the locations of aberrant electrical activity in accordance with the teachings of various references cited herein.

In versions where cylindraceous body (156) is formed of an electrically conductive material to provide RF electrical energy for tissue ablation, an electrically insulating material may be interposed between cylindraceous body (156) and EP mapping microelectrodes (138) to thereby electrically isolate EP mapping microelectrodes (138) from cylindraceous body (156). EP mapping microelectrodes (138) may be constructed and operable in accordance with the teachings of various patent references cited herein. While only one EP mapping microelectrode (138) is shown, distal tip member (142) may include two or more EP mapping microelectrodes (138). Alternatively, distal tip member (142) may lack EP mapping microelectrodes (138) altogether.

Distal tip base (144) defines a central aperture configured to provide a path for communication of irrigation fluid to the hollow interior of distal tip member (142). Distal tip base (144) forms an annular shoulder that the proximal edge of distal tip member (142) may abut. Distal tip member (142) also defines a lateral notch that is configured to receive a proximally extending tab of distal tip member (142). As shown in FIGS. 3-4, distal circuit disk (146) is positioned proximal to distal tip base (144). Distal circuit disk (146) includes circuitry that is operable to communicate RF electrical energy to distal tip member (142) via the proximally extending tab of distal tip member (142). In versions where one or more EP mapping microelectrodes (138) are included, distal circuit disk (146) may also include circuitry that is operable to communicate EP mapping signals from EP mapping electrodes (138).

In some versions, distal circuit disk (146) further includes one or more transmission coils. Such transmission coils may provide wireless communication of signals (e.g., EP mapping signals from microelectrodes (138)) to one or more complementary coils that are proximal to distal circuit disk (146). In addition, or in the alternative, such transmission coils may provide wireless communication of RF electrical energy from one or more complementary coils that are proximal to distal circuit disk (146) to distal tip member (142). In versions where coils are incorporated into distal circuit disk (146) and one or more other layers that are proximal to force sensor assembly (148), such coils may thus enable wireless communication of electrical signals across force sensor assembly (148) without requiring wires, vias, or other electrically conductive structures to pass longitudinally across force sensor assembly (148).

In some versions, distal circuit disk (146) includes at least one transmission coil (TX) that is paired with receiving coil (RX) of position sensor assembly (150) to detect strain being applied to force sensor assembly (148) so as to determine the contact force applied to distal tip (142). Some other versions of distal circuit disk (146) may simply omit a TX coil.

Force sensor assembly (148) is positioned proximal to distal circuit disk (146) and is configured to sense external forces that impinge against distal tip member (142). When distal tip (142) encounters external forces (e.g., when distal tip (142) is pressed against tissue), those external forces are communicated from distal tip (142) to distal tip base (144), to distal circuit disk (146), and to force sensor assembly (148) such that strain gauge may generate a suitable signal corresponding to the magnitude and direction of the external force. The signals from force sensor assembly (148) may be communicated through vias or other structures in the layers that are proximal to force sensor assembly (148), eventually reaching first driver module (14) of console (12) via cable (30). First driver module (14) may process the strain signals in accordance with any suitable fashion as would be apparent to one of ordinary skill in the art in view of the teachings herein. By way of example only, console (12) may provide audible feedback to alert the physician (PH) when force sensor assembly (148) indicates that distal tip member (142) is encountering forces over a predetermined threshold, to thereby prevent the physician (PH) from unwittingly damaging a cardiovascular anatomical structure with distal tip member (142).

Position sensor assembly (150) may generate signals indicating the position and orientation of end effector (140) in three-dimensional space with substantial precision. Position sensor assembly (150) includes a plurality of panels (151), each including an RX coil that is operable to generate position-indicative electrical signals in response to the alternating magnetic fields generated by field generators (20). Each RX coil may be formed by electrical traces to define an electrical coil or antenna to receive radiofrequency signals emitted by external transmitters TX coils (e.g., three TX coils provided by field generators (20) positioned external of the patient (PA) body and emitting discrete radiofrequencies) such that the location and orientation of each RX coil can be determined with respect to the TX coils provided by field generators (20). The signals from position sensor assembly (150) may be communicated through vias or other structures in the layers that are proximal to strain position sensor assembly (150), eventually reaching first driver module (14) of console (12) via cable (30).

A central annular body of position sensor assembly (150) defines a central aperture configured to provide a path for communication of irrigation fluid to the hollow interior of distal tip member (142). In versions where central annular body of position sensor assembly includes wireless communication coils, such wireless communication coils may be further coupled with vias or other structures in the layers that are proximal to strain position sensor assembly (150), thereby providing a path for electrical communication with first driver module (14) of console (12) via cable (30).

In the present example, each distal spacer (153) is generally shaped like a disk, with a pair of chordal cutouts angularly offset from each other by 90 degrees. These cutouts are sized and configured to accommodate a respective panel (151) of position sensor assembly (150), thereby allowing panels (151) to be radially interposed between distal spacer stack (152) and sheath (122). Each distal spacer (153) also includes a pair of cable notches that are angularly offset from each other by 180 degrees. These cable notches are configured to receive a respective distal end portion (174, 164) of push-pull cables (170, 172). Each distal spacer (153) further includes a central aperture configured to provide a path for communication of irrigation fluid to the hollow interior of distal tip member (142).

Each proximal spacer (154) is shaped like a disk, with three apertures formed therethrough. A central aperture is configured to provide a path for communication of irrigation fluid to the hollow interior of distal tip member (142). The side apertures are sized and configured to receive proximal portions (162, 172) of a respective push-pull cable (160, 170).

As noted above and as shown in FIGS. 1 and 3, cable (30) couples catheter assembly (100) with drive system (10). As shown in FIG. 4, wires (32) of cable (30) extend along the length of catheter (120) to reach the proximal-most proximal spacer (154). Wires (32) may thus be contained within sheath (122). Wires (32) may be physically and electrically coupled with the proximal-most proximal spacer (154) in any suitable fashion.

As also noted above, catheter assembly (100) is configured to enable irrigation fluid to be communicated from fluid source (42) to catheter (120) via fluid conduit (40), thereby providing expulsion of the irrigation fluid via openings (158) of distal tip member (142). In the present example, the fluid path for the irrigation fluid includes an irrigation tube (180), which is shown in FIGS. 4-5. The proximal end of irrigation tube (180) is coupled with fluid conduit (40) (e.g., at handle (110) of catheter assembly (100)). Irrigation tube (180) extends along the length of catheter (120) to reach end effector (140). In some versions, irrigation fluid may be communicated from the distal end of irrigation tube (180) through the central passageway formed by the aligned by the above-mentioned central apertures, ultimately reaching the interior of distal tip member (142) via aperture (218) of distal tip base (144).

III. EXAMPLE OF ELECTRODE AND SENSOR ASSEMBLY FOR END EFFECTOR OF CATHETER ASSEMBLY

End effectors of EP mapping or ablation catheters may include various kinds of sensors that are configured to sense conditions associated with tissue that is being contacted by the end effector. Such sensors may include force sensors, temperature sensors, impedance sensors, or other kinds of sensors. In conventional EP mapping or ablation catheters, such sensors may be spaced away from EP mapping electrodes (e.g., microelectrodes (138)) or ablation electrodes. By being spaced away from EP mapping electrodes or ablation electrodes, data acquired through such sensors might not necessarily provide an entirely accurate representation of the conditions associated with the precise location where the tissue is being contacted by a given electrode. It may therefore be desirable to provide an end effector where a sensor is positioned and operable to provide data that is in fact an accurate representation of the conditions associated with the precise location where the tissue is being contacted by a given electrode. To that end, FIGS. 6-7 show an example of an electrode and sensor assembly (200) that may be incorporated into an end effector such as end effector (140).

Figure 6:
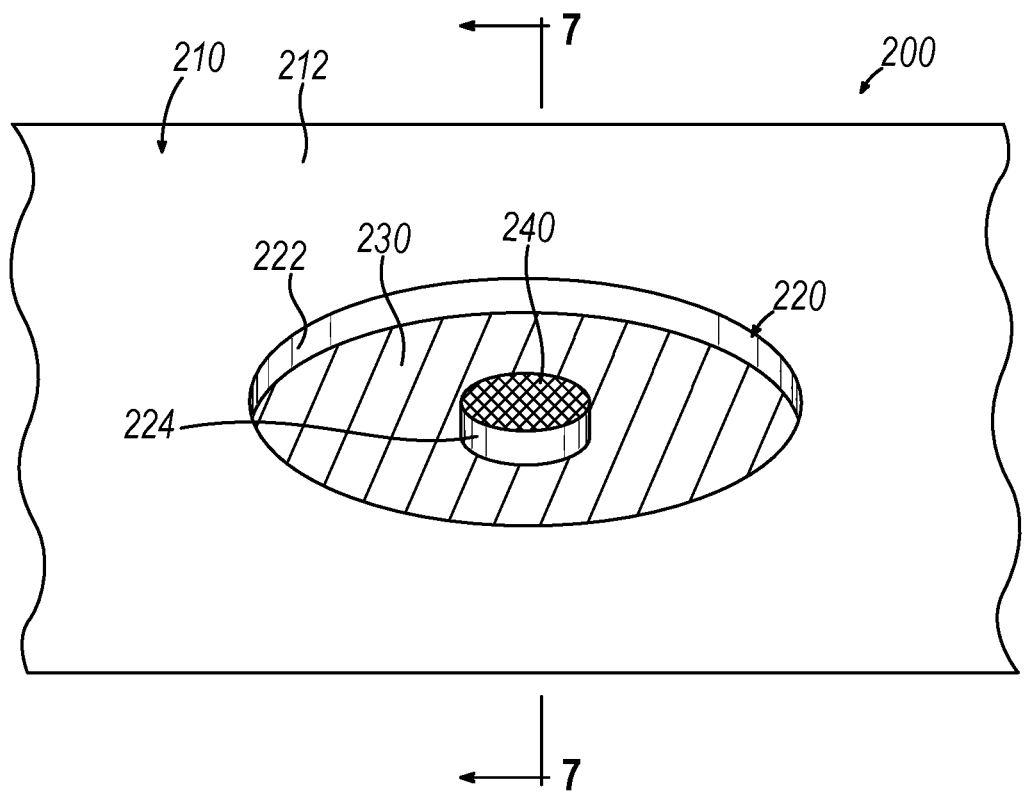
FIG. 6 depicts an example of an electrode and sensor assembly that may be incorporated into an end effector of the catheter of FIG. 1.
Figure 7:
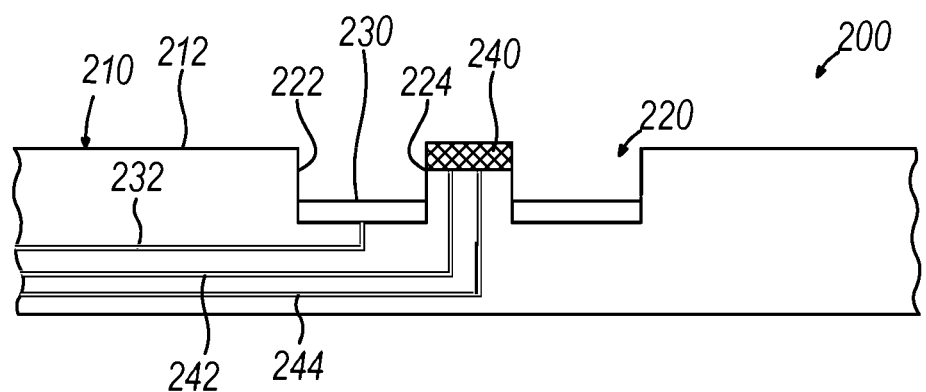
FIG. 7 depicts a cross-sectional view of the electrode and sensor assembly of FIG. 6, taken along line 7-7 of FIG. 6.

As shown in FIGS. 6-7, electrode and sensor assembly (200) of this example includes a base structure (210) that defines a recess (220) in an outer surface (212). By way of example only, base structure (210) may form part of a structure that is an alternative to cylindraceous body (156) of distal tip member (142) of end effector (140). While base structure (210) is shown as being substantially flat, base structure (210) may alternatively have a curvature (e.g., to form a dome tip or other non-flat shape). While only one recess (220) is shown in base structure (210) in FIGS. 6-7, base structure (210) may have several recesses (220) and associated features as will be described in greater detail below. Base structure (210) may also define a plurality of openings, similar to openings (158), to allow communication of irrigation fluid, blood, or other fluids through base structure (210). By way of example only, base structure (210) may include conventional flex circuit materials (e.g., polyimide), nitinol or other metallic materials, or any other suitable kind(s) of material(s) as will be apparent to those skilled in the art in view of the teachings herein.

Recess (220) includes a sidewall (222). While recess (220) is circular in the present example, recess (220) may instead have any other suitable shape, including but not limited to square, hexagonal, etc. An electrode (230) is positioned at the bottom of recess (220), such that electrode (230) is recessed relative to outer surface (212) of base structure (210). In some instances, electrode (230) is an EP mapping electrode (e.g., like EP mapping microelectrode (138)), such that electrode (230) is configured to pick up electrical potentials from tissue that comes into contact with electrode (230). In addition, or in the alternative, electrode (230) may serve as an ablation electrode, such that electrode (230) is configured to ablate tissue that is contacting electrode (230) when electrode (230) is activated with RF energy. Some versions of electrode and sensor assembly (200) may include a combination of one or more electrodes (230) that are used for EP mapping and one or more electrodes (230) that are used for ablation.

In the present example, a sensor (240) is positioned at the center of electrode (230). Sensor (240) is offset from electrode (230) via a sidewall (224), such that sensor (240) is elevated above electrode (230). In some versions, sensor (240) is at the same height as outer surface (212) of base structure (210). In some other versions, sensor (240) is recessed relative to outer surface (212) of base structure (210) but not as recessed as electrode (230). In still other versions, sensor (240) protrudes outwardly relative to outer surface (212) of base structure (210). While sensor (240) is shown as being positioned entirely atop sidewall (224), some versions of sensor (240) may include at least a portion of sensor (240) being positioned along sidewall (224) (e.g., such that a portion of sensor (240) faces sidewall (222) of recess (220). In such versions, even portions of sensor (240) that are positioned along sidewall (224) may still be brought into contact with tissue.

With recess (220) being circular in the present example, and with sensor (240) and sidewall (224) being positioned at the axial center of recess (220) and electrode (230), electrode (230) has an annular shape in this example, such that electrode (230) surrounds the outer perimeter of sidewall (224). As another merely illustrative example, sensor (240) may be positioned immediately adjacent to the outside of electrode (230). Alternatively, any other suitable positioning and relationships may be utilized.

During use of an end effector that incorporates electrode and sensor assembly (200) as described herein, electrode and sensor assembly (200) may be pressed against tissue (e.g., in a chamber of the heart (H), in a pulmonary vein, etc.) such that electrode (230) and sensor (240) contact the tissue simultaneously. In the present example, the tissue contacting surface of electrode (230) is recessed relative to outer surface (212) of base structure (210), such that tissue may prolapse into recess (220) or otherwise enter recess (220) in order to contact electrode (230). In some other versions, the tissue contacting surface of electrode (230) is substantially flush with outer surface (212) of base structure (210). In such versions, the tissue contacting surface of sensor (240) may be flush with the tissue contacting surface of electrode (230); or be elevated relative to the tissue contacting surface of electrode (230). As another merely illustrative example, the tissue contacting surface of electrode (230) may be elevated relative to outer surface (212) of base structure (210). Again, in such versions, the tissue contacting surface of sensor (240) may be flush with the tissue contacting surface of electrode (230); or be elevated relative to the tissue contacting surface of electrode (230). It should be understood, however, that tissue does not necessarily need to contact electrode (230) in order for electrode (230) to pick up signals from the tissue. For instance, signals may be communicated through fluid (e.g., blood, saline, etc.) that is interposed between the tissue and electrode (230) when the tissue is brought within sufficient proximity of electrode (230).

As shown in FIG. 7, a conduit (232) is coupled with electrode (230); while two conduits (242, 244) are coupled with sensor (240). In some other versions, electrode (230) has two conduits (232). Conduits (232, 242, 244) may take various forms, including but not limited to wires, conductive traces, etc. Conduits (232, 242, 244) may ultimately be in communication with console (12) via cable (30). Console (12) may thus be operable to receive EP mapping signals from electrode (230) via conduit (232) and cable (30), provide RF energy to electrode (230) via conduit (232) and cable (30), or receive data from sensor (240) via conduits (242, 244) and cable (30). Various suitable ways in which conduits (232, 242, 244) may be integrated into base structure (210), or otherwise be supported by base structure (210), will be apparent to those skilled in the art in view of the teachings herein.

Sensor (240) may be operable to sense various kinds of conditions. By way of example only, sensor (240) may be operable to sense the temperature of tissue that is being contacted by sensor (240). In such versions, sensor (240) may be thermally isolated relative to electrode (230), such that sensor (240) only measures the temperature of tissue that is being contacted by sensor (240) without measuring the temperature of electrode (230). By way of example only, versions of sensor (240) that are operable to sense temperature may include a thermocouple or any other suitable kind of temperature sensor as will be apparent to those skilled in the art in view of the teachings herein. In versions where electrode (230) is operable to apply RF ablation energy to the tissue, temperature data picked up by sensor (240) may be processed by console (12) to modulate the delivery of RF energy by electrode (230) in real time. For instance, such temperature data may be used to determine when the tissue has been sufficiently ablated, to prevent the tissue from being overheated during ablation. In such cases, console (12) may track the tissue impedance data from sensor (240) in real time during delivery of the RF energy by electrode (230). Once the tissue temperature data indicates that a certain threshold value has been reached, console (12) may cease or otherwise reduce delivery of RF energy by electrode (230). In addition, or in the alternative, console (12) may utilize tissue temperature data from sensor (240) for other purposes as will be apparent to those skilled in the art in view of the teachings herein.

By way of further example only, sensors (240) and electrodes (230) may be utilized together to sense the impedance of tissue that is being contacted simultaneously by sensors (240) and electrodes (230). Such impedance values may be used to identify contact between tissue and sensors (240) and electrodes (230). For instance, before sensors (240) and electrodes (230) are in contact with tissue, and while one or both of sensors (240) and electrodes (230) is/are in contact with blood, the sensed impedance value may be relatively low. Once sensors (240) and electrodes (230) are in contact with tissue, the sensed impedance value may substantially increase. Thus, a spike in impedance sensed by sensors (240) and electrodes (230) may indicate contact between sensors (240) and electrodes (230) and tissue. This may further be understood to indicate contact between tissue and the electrode (230) that is adjacent to sensor (240). By utilizing sensors (240) and electrodes (230) that are so closely positioned in relation to each other, end effector (140) with electrode and sensor assembly (200) may provide substantially greater sensitivity to detecting tissue contact as compared to an end effector that senses impedance by using one electrode on the end effector in cooperation with an external electrode (e.g., a patch adhered to the patient's skin).

To the extent that the impedance of tissue varies based on the delivery of RF ablation energy to the tissue, in versions where electrode (230) is operable to apply RF ablation energy to the tissue, the tissue impedance data may be processed by console (12) to modulate the delivery of RF energy by electrode (230) in real time. For instance, such tissue impedance data may be used to determine when the tissue has been sufficiently ablated, to prevent the tissue from being overheated during ablation. In such cases, console (12) may track the tissue impedance data from sensor (240) in real time during delivery of the RF energy by electrode (230). Once the tissue impedance data indicates that a certain threshold value has been reached, console (12) may cease delivery of RF energy by electrode (230). Similarly, console (12) may vary the frequency, amplitude, or other characteristics of the RF energy delivery, based on real time tissue impedance data from sensor (240), before ceasing a suitable form of energy such as direct current (DC) in the form of pulsed direct current bipolar ablation (e.g., irreversible energy ablation or pulsed field ablation) or alternating current (AC) in the form of RF energy delivery.

In addition, or in the alternative, console (12) may utilize tissue impedance data from sensor (240) for other purposes as will be apparent to those skilled in the art in view of the teachings herein.

Figure 8:
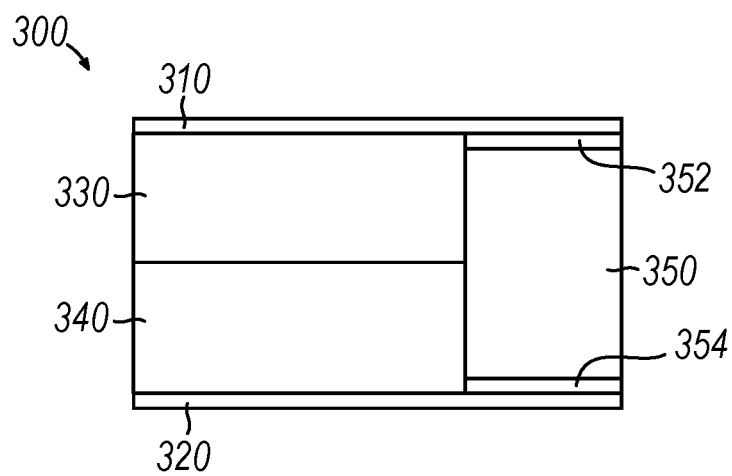
FIG. 8 depicts a side cross-sectional view of an example of a force sensor that may be incorporated into the electrode and sensor assembly of FIG. 6.
Figures 9, 10:
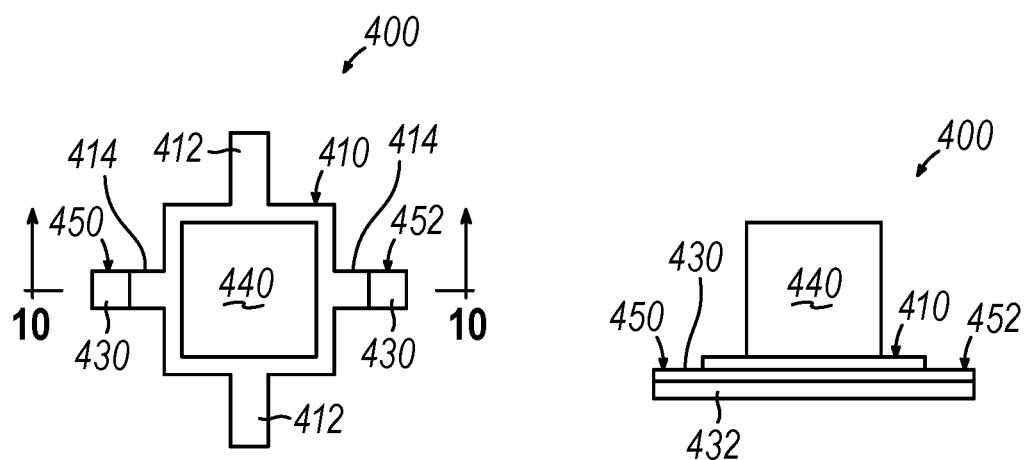
FIG. 9 depicts a top plan view of another example of a force sensor that may be incorporated into the electrode and sensor assembly of FIG. 6.
FIG. 10 depicts a side cross-sectional view of the force sensor of FIG. 9.

As another example, sensor (240) may be operable to sense tissue contacting force (e.g., a normal force imposed by tissue against which sensor (240) is pressed). Such a force sensor may take a variety of different forms. FIG. 8 shows one example of a form that sensor (240) may take. FIGS. 8-12 show some examples of forms that a force sensing version of sensor (240) may take and will be described in greater detail below. Other examples may include a capacitive membrane construction or any other suitable kind of force sensing construction as will be apparent to those skilled in the art in view of the teachings herein.

FIG. 8 shows a force sensor (300) that operates using piezoelectric principles and includes a first electrode layer (310) and a second electrode layer (320). By way of example only, electrode layers (310, 320) may include copper or any other suitable material(s). First electrode layer (310) may be positioned to contact tissue (e.g., like sensor (240) described above); while second electrode layer (320) may positioned at the top of sidewall (224) to provide a foundational support (i.e., mechanical ground) to force sensor (300). In some versions, second electrode layer (320) provides an additional sensing element like sensor (230) described above.

A pair of dielectric layers (330, 340) are interposed between corresponding regions of electrode layers (310, 320); with electrode layers (310,320) being oriented parallel with each other. In particular, a first dielectric layer (330) is positioned directly under first electrode layer (310), and a second dielectric layer (340) is positioned directly over second electrode layer (320), with dielectric layers (330, 340) being directly apposed with each other. By way of example only, each dielectric layer (330, 340) may include a polyimide material. By way of further example only, each dielectric layer (330, 340) may include KAPTON® by DuPont de Nemours, Inc. of Wilmington, Delaware. While a pair of dielectric layers (330, 340) are provided in the present example, some other versions may have just one single dielectric layer (330, 340). It should also be understood that, in versions where first electrode layer (310) is structurally and functionally analogous to sensor (240), and second electrode layer (320) is structurally and functionally analogous to sensor (240), the structure provided by dielectric layers (330, 340) may provide a structural and functional analog to sidewall (224) of electrode and sensor assembly (200). As another merely illustrative example, first electrode layer (310) is structurally and functionally analogous to sensor (240), and second electrode layer (320) may cooperate with dielectric layers (330, 340) to provide a structural and functional analog to sidewall (224) (e.g., such that a separate electrode is provided as an analog to electrode (230)).

A piezoelectric element (350) is interposed between another region of electrode layers (310, 320), laterally adjacent to dielectric layers (330, 340). An upper portion of piezoelectric element (350) is bonded to the underside of first electrode layer (310) by a conductive adhesive (352); while a lower portion of piezoelectric element (350) is bonded to the top side of second electrode layer (320) by a conductive adhesive (354).

In use, force sensor (300) may generate a variable voltage based on the force exerted upon sensor (300) by tissue. In other words, the greater the force imposed on sensor (300) by tissue, the larger the voltage that will be generated by force sensor (300). In some variations of force sensor (300), both electrode layers (310, 320) may be positioned to contact tissue; and electrode layers (310, 320) may also be operable to sense tissue temperature or tissue impedance. Thus, some versions of sensor (300) may be operable to sense any combination of tissue contact force, tissue temperature, and tissue impedance. As yet another merely illustrative variation, either or both layers (310, 320) may be operable to provide one or both of EP mapping or ablation functionality, like electrode (230).

FIGS. 9-12 shows another example of a form that sensor (240) may take. In particular, FIGS. 9-12 show a force sensor (400) that includes a first body (410) with a first pair of opposing arms (412) and a second pair of opposing arms (414). Arms (412) are spaced angularly apart from arms (414) by 90 degrees. Arms (412) have a greater length than arms (414) in this example. By way of example only, first body (410) may include gold or chromium. A cube-shaped mass (440) is positioned on top of the central region of first body (410) and is bonded thereto. Mass (440) is positioned to contact tissue, such that mass (440) will directly receive forces imposed by the contacted tissue; and force sensor (400) will generate a signal indicating the forces imposed on mass (440). While mass (440) is shown and described as a cube in the present example, mass (440) may have any other suitable shape as will be apparent to those skilled in the art in view of the teachings herein.

A first layer (430) is positioned underneath at least a portion of first body (410). First layer (430) includes a first arm region (450) protruding outwardly relative to one arm (414) of first body (410); and a second arm region (452) protruding outwardly relative to the other arm (414) of first body (410). Arm regions (450, 452) are thus exposed relative to arms (414). By way of example only, first layer (430) may include doped silicon. A second layer (432) is positioned underneath first layer (430). For instance, second layer (432) may span across the entire underside of first layer (430). By way of example only, second layer (432) may include silicon.

Figure 11:
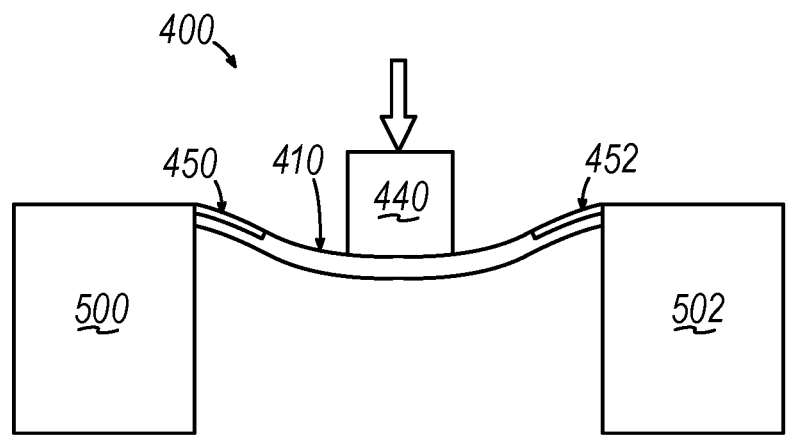
FIG. 11 depicts a side elevational view of the force sensor of FIG. 9, with a mass of the force sensor encountering a perpendicularly oriented force.
Figure 12:
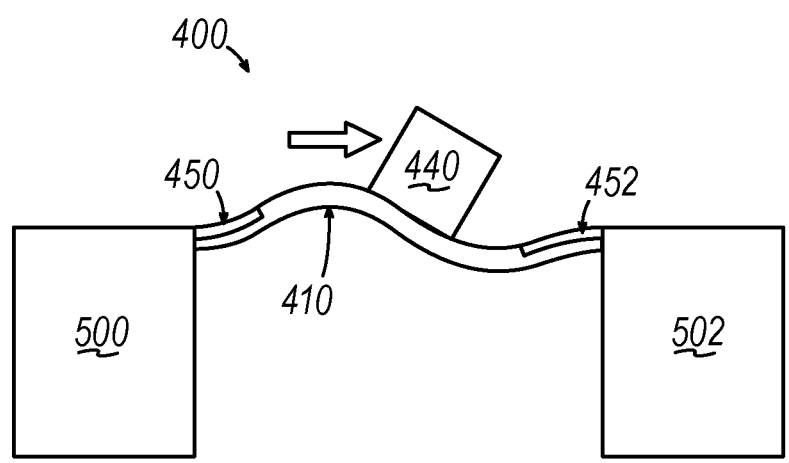
FIG. 12 depicts a side elevational view of the force sensor of FIG. 9, with a mass of the force sensor encountering a laterally oriented force.

As shown in FIGS. 11-12, layers (430, 432) may be secured to two support structures (500, 502), such that first arm region (450) is positioned adjacent to a first support structure (500) and second arm region (452) is positioned adjacent to second support structure (502). Support structures (500, 502) may be supported on the top of sidewall (224), such that support structures (500, 502) provide a foundational support (i.e., mechanical ground) to force sensor (400). Alternatively, support structures (500, 502) may be positioned on outer surface (212) of base structure (210) somewhere near electrode (230) but not on sidewall (224). By way of further example only, support structures (500, 502) may be defined by outer surface (212) of base structure (210) (e.g., such that support structures (500, 502) are not separate components that are secured to outer surface (212) of base structure (210)); mass (440) may be positioned above the central region of electrode (230) (e.g., in place of sensor (240)); and arms (412, 414) may span over a space above electrode (230) to support mass (440) above the central region of electrode (230). Other suitable ways in which force sensor (400) may be integrated into electrode and sensor assembly (200), or otherwise integrated into end effector (140), will be apparent to those skilled in the art in view of the teachings herein.

FIG. 11 shows force sensor (400) receiving a force that is generally perpendicular, deforming the central region of first body (410), and both arm regions (450, 452) downwardly. In other words, force sensor (400) is encountering a normal deflection in FIG. 11. The perpendicularly oriented force (p) may be measured using the following equation:

$$p=(\Delta R_1/R_1+\Delta R_2/R_2)/k_p$$

where p=the magnitude of the perpendicularly oriented force;
$R_1$=the resistance of first layer (430) at first arm region (450);
$R_2$=the resistance of first layer (430) at second arm region (452); and
$k_p$=a conversion constant for normal forces.

FIG. 12 shows force sensor (400) receiving a force that is generally transversely oriented, deforming first arm region (450) upwardly and second arm region (452) downwardly. In other words, force sensor (400) is encountering a shear deflection in FIG. 12. The transversely oriented force (T) may be measured using the following equation:

$$T=(\Delta R_1/R_1-\Delta R_2/R_2)/k_s$$

where T=the magnitude of the transversely oriented force;
$R_1$=the resistance of first layer (430) at first arm region (450);
$R_2$=the resistance of first layer (430) at second arm region (452); and
$k_s$=a conversion constant for shear forces.

Of course, in real-world scenarios, forces imposed on sensor (400) may include a combination of a perpendicularly oriented component and a transversely oriented component. It should be understood that sensor (400) may detect two axis forces to derive a force direction vector. Other variations may be simplified to only measure normal forces (e.g., without measuring shear/transverse forces).

In versions where sensor (240) is operable to measure force (e.g., where sensor (240) is in the form of sensor (300), in the form of sensor (400), or in some other form), the force data from sensor (240) may be used in various ways. For instance, console (12) may drive display (18) to provide visual feedback to the physician (PH) to indicate the amount of force encountered by sensor (240), which may reflect the force at which the corresponding electrode (230) is being pressed against tissue. In cases where the force exceeds a threshold value (e.g., a value associated with undesirable trauma to tissue due to pressing against the tissue with too much force), console (12) may further provide an audible or visual indication to the physician (PH) to alert the physician (PH) that they are applying too much force against the tissue. In addition, or in the alternative, force data from sensor (240) may be processed by console (12) to modulate the delivery of RF energy by electrode (230) in real time. For instance, console (12) may prevent an electrode (230) from being activated with RF energy until force data from the corresponding sensor (240) indicates that sensor (240) and electrode (230) are being pressed against tissue with sufficient force. As yet another example, force data from sensor (240) may be used (e.g., in combination with other measurements such as power and duration of RF application) to estimate the size of a lesion that is created by an ablation procedure using electrode (230). Alternatively, force data from sensor (240) may be used for any other suitable purposes as will be apparent to those skilled in the art in view of the teachings herein, including but not limited to providing a warning when force exceeds a threshold (e.g., to avoid inadvertent perforation of tissue with end effector (140)). In versions where end effector (140) is operable to measure temperature, since readings of force measurement sensors can be affected by temperature (e.g., due to expansion/contraction of elements, etc.), the temperature measurements may be used to provide error corrections in force measurements.

In the present example, electrode (230) and sensor (240) are constructed integrally together. In other words, electrode (230) and sensor (240) may be constructed together simultaneously in the same process. In some other versions, electrode (230) and sensor (240) may be constructed separately and then subsequently assembled together (e.g., through a lamination process or other process).

It should be understood from the foregoing that the configuration of electrode and sensor assembly (200) allows each sensor (240) to provide highly localized data that is spatially relevant to a corresponding electrode (230). Such highly localized data may be more meaningful than data that would be acquired from a sensor that is further spatially displaced from electrode (230). For instance, to the extent that a conventional ablation catheter may provide a single contact force sensor providing contact force data indicating a contact force on the entire tip of the end effector (which may include more than one ablation electrode), an ablation catheter that includes a plurality of electrode and sensor assemblies (200) on the end effector may provide several separate measurements of contact force data, on a per-electrode (230) basis. It should also be understood that the relatively small size of each sensor (240) may promote full contact between sensor (240) and tissue; as contrasted against conventional catheters with sensors that are so large that, during use of such catheters, the tissue contacts only a portion of the sensor. The full contact between sensor (240) and tissue may provide data that is more reliable and meaningful than data that would be acquired by a larger sensor that only has a portion in contact with tissue.

IV. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a catheter body having a distal end, the catheter body being sized and configured to fit within regions of a cardiovascular system; and (b) an end effector at the distal end of the catheter body, the end effector being sized and configured to fit within regions of a cardiovascular system, the end effector including: (i) an end effector body member having an outer surface, (ii) an electrode, the electrode having a tissue contact surface, and (iii) a sensor, the sensor having a tissue contact surface, the sensor being configured to sense at least one condition associated with tissue contacting the tissue contact surface of the sensor, the tissue contact surface of the sensor being configured to protrude relative to one or both of the outer surface of the end effector body member or the tissue contact surface of the electrode.

Example 2

The apparatus of Example 1, the end effector defining a dome tip.

Example 3

The apparatus of any one or more of Examples 1 through 2, the electrode being operable to pick up electrical potentials from tissue contacting the tissue contact surface of the electrode.

Example 4

The apparatus of any one or more of Examples 1 through 3, the electrode being operable to ablate tissue contacting the tissue contact surface of the electrode.

Example 5

The apparatus of Example 4, the electrode being operable to apply one or more of pulsed direct current bipolar ablation or radiofrequency energy to tissue contacting the tissue contact surface of the electrode, to thereby ablate the tissue contacting the tissue contact surface of the electrode.

Example 6

The apparatus of any one or more of Examples 1 through 5, the end effector body member defining a recess.

Example 7

The apparatus of Example 6, the electrode being positioned in the recess.

Example 8

The apparatus of Example 7, the tissue contact surface of the electrode being recessed relative to the outer surface of the end effector body.

Example 9

The apparatus of any one or more of Examples 1 through 8, the electrode having an annular shape defining a radial center.

Example 10

The apparatus of Example 9, the electrode being positioned at the radial center of the electrode.

Example 11

The apparatus of any one or more of Examples 1 through 10, the sensor having a circular shape.

Example 12

The apparatus of any one or more of Examples 1 through 11, the end effector body further including a first sidewall and a second sidewall, the electrode being positioned between the first sidewall and the second sidewall.

Example 13

The apparatus of Example 12, the second sidewall facing the first sidewall.

Example 14

The apparatus of any one or more of Examples 12 through 13, the first and second sidewalls each having a cylindraceous profile.

Example 15

The apparatus of any one or more of Examples 12 through 14, the sensor being positioned atop the second sidewall, the second sidewall being an inner side wall.

Example 16

The apparatus of any one or more of Examples 1 through 15, the sensor being configured to sense temperature of tissue contacting the tissue contact surface of the sensor.

Example 17

The apparatus of Example 16, the electrode being operable to apply radiofrequency energy to tissue contacting the tissue contact surface of the electrode.

Example 18

The apparatus of Example 17, further comprising a control module, the control module being in communication with the sensor and with the electrode, the control module being operable to modulate delivery of radiofrequency energy to the electrode based on temperature data from the sensor.

Example 19

The apparatus of Example 18, the control module being operable to cease delivery of radiofrequency energy to the electrode in response to a sensed temperature value exceeding a threshold value.

Example 20

The apparatus of any one or more of Examples 1 through 19, the sensor being configured to sense impedance of tissue contacting the tissue contact surface of the sensor.

Example 21

The apparatus of Example 20, the electrode being operable to apply one or more of pulsed direct current bipolar ablation or radiofrequency energy to tissue contacting the tissue contact surface of the electrode.

Example 22

The apparatus of Example 21, further comprising a control module, the control module being in communication with the sensor and with the electrode, the control module being operable to modulate delivery of one or more of pulsed direct current bipolar ablation or radiofrequency energy to the electrode based on impedance data from the sensor.

Example 23

The apparatus of Example 22, the control module being operable to cease delivery of radiofrequency energy to the electrode in response to a sensed impedance reaching a threshold value.

Example 24

The apparatus of any one or more of Examples 22 through 23, the control module being operable to vary a voltage and duration of one or more of pulses of direct current bipolar ablation or one or both of frequency or amplitude of radiofrequency energy to the electrode based on impedance data from the sensor.

Example 25

The apparatus of any one or more of Examples 20 through 22, further comprising a control module in communication with the sensor, the control module being configured to: (i) determine whether the sensor is in contact with tissue based on impedance data from the sensor, and (ii) indicate that the sensor is in contact with tissue in response to determining that the sensor is in contact with tissue based on impedance data from the sensor.

Example 26

The apparatus of any one or more of Examples 1 through 25, the sensor being configured to detect force between the tissue contact surface of the sensor and adjacent tissue.

Example 27

The apparatus of Example 26, further comprising a control module, the control module being in communication with the sensor, the control module being configured to determine whether the sensor is in contact with tissue based on force data from the sensor.

Example 28

The apparatus of Example 27, the electrode being operable to apply one or more of pulsed direct current bipolar ablation or radiofrequency energy to tissue contacting the tissue contact surface of the electrode.

Example 29

The apparatus of Example 28, the control module being operable to modulate delivery of one or more of pulsed direct current bipolar ablation or radiofrequency energy to the electrode until force data from the sensor indicates contact between the sensor and tissue.

Example 30

The apparatus of any one or more of Examples 28 through 29, the control module being operable to prevent delivery of one or more of pulsed direct current bipolar ablation or radiofrequency energy to the electrode until force data from the sensor indicates contact between the sensor and tissue.

Example 31

The apparatus of any one or more of Examples 26 through 30, the force sensor including a piezoelectric element.

Example 32

The apparatus of Example 31, the force sensor further including a first electrode layer and a second electrode layer, the piezoelectric element being interposed between a first associated region between the first and second electrode layers.

Example 33

The apparatus of Example 32, the force sensor further including a pair of dielectric layers adjacent to the piezoelectric element, the dielectric layers being interposed between a second associated region between the first and second electrode layers.

Example 34

The apparatus of any one or more of Examples 26 through 33, the force sensor including a pair of arms secured to a corresponding pair of support structures, the force sensor being configured to sense force based on deformation of the arms.

Example 35

The apparatus of any one or more of Examples 1 through 34, further comprising a position sensor, the position sensor being operable to generate signals indicating a real-time position of the end effector in three-dimensional space.

Example 36

The apparatus of Example 35, the position sensor being located in the end effector.

Example 37

The apparatus of any one or more of Examples 1 through 36, the end effector further comprising: (i) a plurality of electrodes including the electrode, and (ii) plurality of sensors including the sensor.

Example 38

An apparatus, comprising: (a) a catheter body having a distal end, the catheter body being sized and configured to fit within regions of a cardiovascular system; and (b) an end effector at the distal end of the catheter body, the end effector being sized and configured to fit within regions of a cardiovascular system, the end effector including: (i) an end effector body member having an outer surface, (ii) an electrode, the electrode having a tissue contact surface, the tissue contact surface being recessed relative to the outer surface of the end effector body member, the electrode being operable to perform one or both of: (A) picking up electrical potentials from tissue contacting the tissue contact surface of the annular electrode, or (B) ablating tissue contacting the tissue contact surface of the annular electrode, and (iii) a sensor, the sensor having a tissue contact surface, the sensor being configured to sense at least one condition associated with tissue contacting the tissue contact surface of the sensor, the tissue contact surface of the sensor being configured to protrude relative to the tissue contact surface of the electrode.

Example 39

An apparatus, comprising: (a) a catheter body having a distal end, the catheter body being sized and configured to fit within regions of a cardiovascular system; and (b) an end effector at the distal end of the catheter body, the end effector being sized and configured to fit within regions of a cardiovascular system, the end effector including: (i) an end effector body member having an outer surface, (ii) an electrode, the electrode having a tissue contact surface and a central region, the tissue contact surface of the electrode being exposed relative to the outer surface of the end effector body member, the electrode being operable to perform one or both of: (A) picking up electrical potentials from tissue contacting the tissue contact surface of the annular electrode, or (B) ablating tissue contacting the tissue contact surface of the annular electrode, and (iii) a sensor positioned in the central region of the electrode, the sensor having a tissue contact surface, the sensor being configured to sense at least one condition associated with tissue contacting the tissue contact surface of the sensor, the tissue contact surface of the sensor being exposed relative to the outer surface of the end effector body member and relative to the tissue contact surface of the electrode.

Example 40

An apparatus, comprising: (a) a catheter body having a distal end, the catheter body being sized and configured to fit within regions of a cardiovascular system; and (b) an end effector at the distal end of the catheter body, the end effector being sized and configured to fit within regions of a cardiovascular system, the end effector including: (i) an end effector body member having an outer surface, (ii) an annular electrode, the electrode having a tissue contact surface, the electrode being operable to perform one or both of: (A) picking up electrical potentials from tissue contacting the tissue contact surface of the annular electrode, or (B) ablating tissue contacting the tissue contact surface of the annular electrode, and (iii) a sensor positioned in a radially central region of the annular electrode, the sensor having a tissue contact surface, the sensor being configured to sense at least one condition associated with tissue contacting the tissue contact surface of the sensor, the tissue contact surface of the sensor being exposed relative to the tissue contact surface of the electrode.

V. MISCELLANEOUS

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein, in its entirety.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein, in its entirety is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, in its entirety, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a catheter body having a distal end, the catheter body being sized and configured to fit within regions of a cardiovascular system; and
   (b) an end effector at the distal end of the catheter body, the end effector being sized and configured to fit within regions of a cardiovascular system, the end effector including:
      (i) an end effector body member having an outer surface and a recess, the recess comprising a bottom surface, an outer sidewall, and an inner sidewall, the outer and inner sidewalls extending from the bottom surface of the recess,
      (ii) an electrode positioned in the recess of the end effector body member such that a bottom surface of the electrode is disposed on the bottom surface of the recess, the electrode having a tissue contact surface which is opposite the bottom surface of the electrode, the tissue contact surface facing an outward direction from the recess, the electrode surrounded by the outer sidewall, and
      (iii) a sensor positioned on the inner sidewall, the sensor having a tissue contact surface also facing the outward direction from the recess, the sensor being configured to sense at least one condition associated with tissue contacting the tissue contact surface of the sensor, the sensor elevated by the inner sidewall such that the tissue contact surface of the sensor protrudes relative to one or both of the outer surface of the end effector body member or the tissue contact surface of the electrode.

2. The apparatus of claim 1, the electrode being operable to pick up electrical potentials from tissue contacting the tissue contact surface of the electrode.

3. The apparatus of claim 1, the electrode being operable to ablate tissue contacting the tissue contact surface of the electrode.

4. The apparatus of claim 1, the tissue contact surface of the electrode being recessed relative to the outer surface of the end effector body.

5. The apparatus of claim 1, the electrode having an annular shape defining a radial center, the sensor being positioned at the radial center of the electrode.

6. The apparatus of claim 1, the sensor being configured to sense temperature of tissue contacting the tissue contact surface of the sensor.

7. The apparatus of claim 6, further comprising a control module, the control module being in communication with the sensor and with the electrode, the electrode being operable to apply radiofrequency energy to tissue contacting the tissue contact surface of the electrode, the control module being operable to modulate delivery of radiofrequency energy to the electrode based on temperature data from the sensor.

8. The apparatus of claim 7, the control module being operable to cease delivery of radiofrequency energy to the electrode in response to a sensed temperature value exceeding a threshold value.

9. The apparatus of claim 1, the sensor being configured to sense impedance of tissue contacting the tissue contact surface of the sensor.

10. The apparatus of claim 9, further comprising a control module, the control module being in communication with the sensor and with the electrode, the electrode being operable to apply one or more of pulsed direct current bipolar ablation or radiofrequency energy to tissue contacting the tissue contact surface of the electrode, the control module being operable to modulate delivery of one or more of pulsed direct current bipolar ablation or radiofrequency energy to the electrode based on impedance data from the sensor.

11. The apparatus of claim 10, the control module being operable to cease delivery of radiofrequency energy to the electrode in response to a sensed impedance reaching a threshold value.

12. The apparatus of claim 10, the control module being operable to vary a voltage and duration of one or more of pulses of direct current bipolar ablation or one or both of frequency or amplitude of radiofrequency energy to the electrode based on impedance data from the sensor.

13. The apparatus of claim 9, further comprising a control module in communication with the sensor, the control module being configured to:
   (i) determine whether the sensor is in contact with tissue based on impedance data from the sensor, and
   (ii) indicate that the sensor is in contact with tissue in response to determining that the sensor is in contact with tissue based on impedance data from the sensor.

14. The apparatus of claim 1, further comprising a control module, the control module being in communication with the sensor, the sensor being configured to detect force between the tissue contact surface of the sensor and adjacent tissue, the control module being configured to determine whether the sensor is in contact with tissue based on force data from the sensor.

15. The apparatus of claim 14, the electrode being operable to apply one or more of pulsed direct current bipolar ablation or radiofrequency energy to tissue contacting the tissue contact surface of the electrode, the control module being operable to perform one or both of:
   (i) modulating delivery of one or more of pulsed direct current bipolar ablation or radiofrequency energy to the electrode until force data from the sensor indicates contact between the sensor and tissue, or
   (ii) preventing delivery of one or more of pulsed direct current bipolar ablation or radiofrequency energy to the electrode until force data from the sensor indicates contact between the sensor and tissue.

16. The apparatus of claim 1, the sensor including a force sensor configured to detect force between the tissue contact surface of the sensor and adjacent tissue, the force sensor including a piezoelectric element.

17. The apparatus of claim 16, the force sensor further including:
   (i) a first electrode layer and a second electrode layer, the piezoelectric element being interposed between a first associated region between the first and second electrode layers, and
   (ii) a pair of dielectric layers adjacent to the piezoelectric element, the dielectric layers being interposed between a second associated region between the first and second electrode layers.

18. The apparatus of claim 1, the sensor including a force sensor configured to detect force between the tissue contact surface of the sensor and adjacent tissue, the force sensor including a pair of arms secured to a corresponding pair of support structures, the force sensor being configured to sense force based on deformation of the arms.

19. An apparatus, comprising:
(a) a catheter body having a distal end, the catheter body being sized and configured to fit within regions of a cardiovascular system; and
(b) an end effector at the distal end of the catheter body, the end effector being sized and configured to fit within regions of a cardiovascular system, the end effector including:
   (i) an end effector body member having an outer surface and a recess, the recess comprising a bottom surface, an outer sidewall, and an in inner sidewall, the outer and inner sidewalls extending from the bottom surface of the recess,
   (ii) an electrode positioned in the recess of the end effector body member such that a bottom surface of the electrode is disposed on the bottom surface of the recess, the electrode having a tissue contact surface which is opposite the bottom surface of the electrode, the electrode surrounded by the outer sidewall, the tissue contact surface facing an outward direction from the recess and being recessed relative to the outer surface of the end effector body member, the electrode being operable to perform one or both of:
      (A) picking up electrical potentials from tissue contacting the tissue contact surface of the electrode, or
      (B) ablating tissue contacting the tissue contact surface of the electrode, and
   (iii) a sensor positioned on the inner sidewall, the sensor having a tissue contact surface also facing the outward direction from the recess, the sensor being configured to sense at least one condition associated with tissue contacting the tissue contact surface of the sensor, the sensor elevated by the inner sidewall such that the tissue contact surface of the sensor protrudes relative to the tissue contact surface of the electrode.

20. An apparatus, comprising:
(a) a catheter body having a distal end, the catheter body being sized and configured to fit within regions of a cardiovascular system; and
(b) an end effector at the distal end of the catheter body, the end effector being sized and configured to fit within regions of a cardiovascular system, the end effector including:
   (i) an end effector electrode body member having an outer surface and a recess, the recess comprising a bottom surface, an outer sidewall and an inner side wall, the outer and inner sidewalls extending from the bottom surface of the recess,
   (ii) an annular microelectrode positioned in the recess of the end effector electrode body member such that a bottom surface of the annular microelectrode is disposed on the bottom surface of the recess, the annular microelectrode having a tissue contact surface opposite the bottom surface of the annular microelectrode and a central region, the tissue contact surface of the annular microelectrode facing an outward direction from the recess, the annular microelectrode surrounded by the outer sidewall and being exposed relative to the outer surface of the end effector electrode body member, the annular microelectrode being operable to perform one or both of:
      (A) picking up electrical potentials from tissue contacting the tissue contact surface of the annular microelectrode, or
      (B) ablating tissue contacting the tissue contact surface of the annular microelectrode, and
   (iii) a sensor positioned on the inner sidewall, the sensor positioned in the central region of the annular microelectrode, the sensor having a tissue contact surface also facing the outward direction from the recess, the sensor being configured to sense at least one condition associated with tissue contacting the tissue contact surface of the sensor, the sensor elevated by the inner sidewall such that the tissue contact surface of the sensor is exposed relative to the outer surface of the end effector electrode body member and relative to the tissue contact surface of the annular microelectrode.

* * * * *